United States Patent
Steinman et al.

(10) Patent No.: US 9,565,853 B2
(45) Date of Patent: Feb. 14, 2017

(54) PERFUSION APPARATUS WITH REDUCED PRESSURE FLUCTUATIONS, AND BUBBLE TRAP

(75) Inventors: Christopher P. Steinman, Sandy, UT (US); Jeffrey S. Louis, Akron, OH (US); Rick W. Walker, Stow, OH (US); Evan D. Shapiro, Chicago, IL (US); Aaron R. Ferber, Chicago, IL (US); Rodney H. Monson, Waukegan, IL (US); John Stark, Bartlett, IL (US); Ross Lockwood, Chicago, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days.

(21) Appl. No.: 13/545,060

(22) Filed: Jul. 10, 2012

(65) Prior Publication Data
US 2014/0017658 A1    Jan. 16, 2014

(51) Int. Cl.
A01N 1/02 (2006.01)
A61M 1/36 (2006.01)
A61M 5/36 (2006.01)

(52) U.S. Cl.
CPC .......... *A01N 1/0247* (2013.01); *A61M 1/3627* (2013.01); *A61M 1/3638* (2014.02); *A61M 5/36* (2013.01)

(58) Field of Classification Search
CPC .... A61M 1/3638; A61M 5/36; A61M 1/3627; A01N 1/0247
See application file for complete search history.

(56) References Cited

U.S. PATENT DOCUMENTS 6,171,484 B1    1/2001   Schnell et al.
7,279,031 B1 *  10/2007  Wright ............... A61M 1/3627
                                                    604/126
(Continued)

FOREIGN PATENT DOCUMENTS

CN    102741668 A    10/2012
DE    103 48 746 A1   3/2005
(Continued)

OTHER PUBLICATIONS

IGL Group, "Waters Advanced Viability Evaluation System: Waves," 2011, pp. 1-12.
Technical Resource Library from Cole-Partner, "Reducing Pulsation," 2011, http://www.coleparmer.com/TechLibraryArticle/632.
Nov. 14, 2014 Written Opinion and International Preliminary Report issued in PCT/US2013/049569.
(Continued)

*Primary Examiner* — Jonathan Hurst
(74) *Attorney, Agent, or Firm* — Oliff PLC

(57) ABSTRACT

An apparatus for separating gas bubbles that may be entrained in perfusate flow prevents such bubbles from continuing downstream and entering an organ or tissue. The apparatus may include a chamber having a top wall, a bottom wall and side walls. The chamber may include an inlet configured to allow at least one of gas and liquid to enter the chamber, an air opening configured to allow at least gas to exit the chamber and a first liquid opening configured to allow at least liquid to exit the chamber. The apparatus may function as an accumulator that reduces or eliminates pulsatility of the liquid flow and pressure. The apparatus may include a minimum volume of gas, initially or through the accumulation of gas, such that flow and pressure fluctuations in the liquid are dampened or eliminated. The apparatus may include a sampling port in a wall of the chamber.

15 Claims, 9 Drawing Sheets

(56) References Cited

U.S. PATENT DOCUMENTS

| | | | |
|---|---|---|---|
| 8,109,284 B2* | 2/2012 | Furey et al. ............. | 137/197 |
| 8,128,740 B2 | 3/2012 | Wright et al. | |
| 2004/0221719 A1* | 11/2004 | Wright et al. ............. | 95/241 |
| 2005/0155427 A1 | 7/2005 | Magers et al. | |
| 2006/0210959 A1 | 9/2006 | Dancu et al. | |
| 2010/0089807 A1 | 4/2010 | Heyes et al. | |

FOREIGN PATENT DOCUMENTS

| | | |
|---|---|---|
| DE | 10 2010 001 605 A1 | 8/2011 |
| EP | 0 553 401 A1 | 8/1993 |
| EP | 1 844 801 A1 | 10/2007 |
| WO | WO 96/30111 A1 | 10/1996 |
| WO | WO 96/41525 A2 | 12/1996 |
| WO | WO 99/64131 A1 | 12/1999 |

OTHER PUBLICATIONS

Jan. 13, 2015 International Preliminary Report on Patentability issued in PCT/US2013/049569.

Mar. 31, 2014 Written Opinion of the International Searching Authority issued in International Patent Application No. PCT/US2013/049569.

Mar. 31, 2014 International Search Report of the International Searching Authority issued in International Patent Application No. PCT/US2013/049569.

Anonymous, "Hall Effect Digital Liquid Level Sensor," Research Disclosure, Mason Publications, Hampshire, Great Britain, May 1, 1985, vol. 253, No. 4 (Abstract).

Sep. 8, 2016 Office Action issued in Chinese Patent Application No. 201380046704.6.

Janaury 13, 2016 Office Action issued in Chinese Patent Application No. 201380046704.6.

\* cited by examiner

STATE 0 (INITIAL STATE)

STATE 1 (FILL STATE)

STATE 2 (NORMAL OPERATING STATE)

STATE 3 (REFILL STATE)

STATE 4 (EMERGENCY STATE)

PERFUSION APPARATUS WITH REDUCED PRESSURE FLUCTUATIONS, AND BUBBLE TRAP

BACKGROUND

Related technical fields include perfusion apparatuses capable of monitoring, sustaining and/or restoring the viability of organ(s) and or tissue for storing and/or transporting the organ(s) or tissue, and in particular, apparatuses that include bubble traps and/or devices to remove entrained gas in a perfusion liquid.

Various perfusion devices developed for storing and/or transporting an organ include, e.g., a bubble trap or similar device for separating gas from a liquid path. For example, U.S. Pat. No. 8,128,740 to Wright et al. (Wright) discloses an example of an organ perfusion apparatus that includes a bubble trap. Wright discloses a bubble trap with an inlet opening, a gas outlet opening and a liquid outlet opening. In the depicted embodiments, the gas outlet opening is located near the top of the bubble trap. Wright discloses that a sensor associated with either an inlet tube port connector or a liquid outlet tube port connector can be used to detect the presence of bubbles. U.S. Patent Application Publication No. 2006/0210959 to Dancu et al. discloses a hemodynamic simulator that provides independent control of pulsatile flow rate and pulsatile pressure. Embodiments include a noise filter for dampening high frequency vibrations created by movements of a peristaltic pump. The noise filter may also serve as a bubble trap, having a container with fluid inlet and outlet ports, and air inlet and outlet ports at or near the top of the container.

It is often desirable to obtain samples of perfusate during the perfusion process to monitor properties of the perfusate, organ and/or tissue. For example, Wright discloses a sample port in a tube that leads to an inlet of a bubble trap.

SUMMARY

For ease of reference herein, the term "organ" will mean organ and/or tissue unless otherwise indicated. Also, for ease of reference, the term "fluid" will mean a gas, a liquid, or a combination thereof unless otherwise indicated.

Perfusion apparatuses may be used for storage, transportation, diagnosis and/or treatment of harvested or engineered organs for transplantation or ex vivo use, and one purpose is to maintain the organ in a viable state. In these apparatuses, a pump is often used to pump perfusate through the apparatus. Pumps that may be used in organ perfusion apparatuses include roller pumps, which have the advantage of minimal components that come into contact with the perfusate. However, the use of roller pumps and other similar pumps often results in pulsatile flow rate and pressure of the perfusate, which may be undesirable. In addition, sample ports in tubing require delicate maneuvering and/or specialized tools to use in view of the small size of the tubing.

Exemplary embodiments of the invention provide a perfusion apparatus that includes a bubble trap that not only removes bubbles, but also dampens pulsatility of the perfusate through, e.g., a configuration in which a minimum volume of gas that is sufficient to dampen the pulsatility of the perfusate is maintained within the bubble trap. In embodiments, sensors are disposed in the bubble trap and configured to detect the level of perfusion liquid in the bubble trap, e.g., to determine whether a minimum volume of gas is present that is sufficient to dampen the pulsatility of the perfusate liquid. The same or other exemplary embodiments include a sampling port within the chamber and configured to allow a clinician to obtain samples of the perfusion liquid directly from the bubble trap, for example by way of a standard syringe with a long "needle" or inlet tube.

Embodiments include an apparatus for separating gas from a liquid and dampening flow rate and pressure fluctuations in the liquid. The apparatus may include a chamber with an air outlet and liquid outlets, wherein the air outlet and the liquid outlets are preferably, but not necessarily, disposed on a same side wall of the chamber in substantially a straight line. The chamber may be configured to release gas from the perfusion liquid while maintaining a minimum volume of gas sufficient to dampen flow rate and pressure fluctuations of the perfusion liquid. A method of perfusing an organ or tissue includes flowing a perfusion liquid into a chamber under fluctuating flow rate and pressure, maintaining at least a minimum volume of gas in the chamber sufficient to dampen flow rate and pressure fluctuations of the perfusion liquid, allowing the perfusion liquid with reduced flow rate and pressure fluctuations to flow out of the chamber, and perfusing the organ or tissue with reduced flow rate and pressure fluctuation liquid.

Embodiments include an apparatus for separating gas from a perfusion liquid that includes a bubble trap and a liquid level sensor. The liquid level sensor may be used, for example, to determine, and optionally signal a controller, when a liquid level in the bubble trap is outside of an optimal range.

A method of priming a perfusion apparatus for perfusing an organ or tissue includes flowing a perfusion liquid through a chamber and into the organ or tissue and sensing if the perfusion liquid reaches a preferred operational level. While the perfusion liquid flows into the chamber, the air outlet may be open. If perfusion liquid is sensed to reach the preferred operational level, the apparatus may shut off the air outlet.

Embodiments include an apparatus for separating gas from a perfusion liquid for perfusing an organ or tissue, including a chamber that includes an inlet, a liquid outlet and a sampling port configured to allow a liquid sample to be continuously or periodically withdrawn from the chamber. A method of perfusing an organ or tissue may include flowing a perfusion liquid through a bubble trap to vasculature of the organ or tissue and continuously or periodically withdrawing a liquid sample directly from the bubble trap.

BRIEF DESCRIPTION OF THE DRAWINGS

In FIGS. 5A-5E, "NO" is defined as "normally open" and "NC" is defined as "normally closed."

DETAILED DESCRIPTION OF EMBODIMENTS

Figure 1:
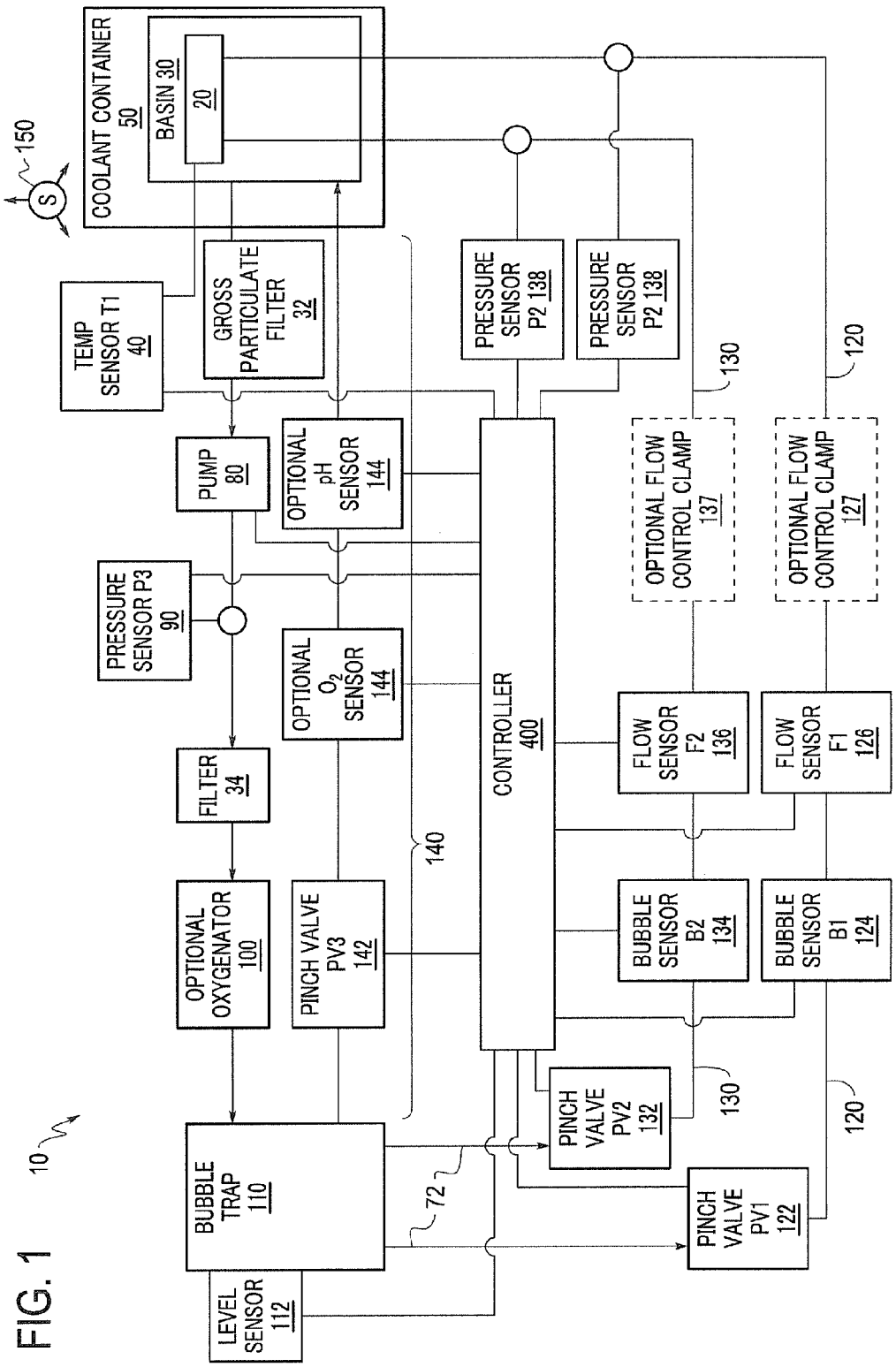
FIG. 1 is a schematic diagram of an exemplary organ perfusion apparatus according to an embodiment of the invention.

The following exemplary implementations refer to a perfusion apparatus, transport apparatus, and/or storage apparatus for an organ. It should be appreciated that, although the exemplary systems and methods according to this disclosure may be applicable to specific applications, the depictions and/or descriptions included in this disclosure are not intended to be limited to any specific application.

According to exemplary implementations, a bubble trap for separating gas from a liquid is provided. The bubble trap may include a chamber having a top wall, a bottom wall, and side walls. The chamber may include an inlet, preferably located in or near the bottom wall (e.g., in a bottom or side wall) configured to allow fluid to enter the chamber. The chamber may have an air opening located between the top wall and the bottom wall, for example in a side wall substantially midway between the top and bottom wall, and configured to allow at least gas to exit the chamber. The chamber may have a first liquid opening, again preferably located in or near the bottom wall (e.g., in a bottom or side wall), configured to allow at least liquid to exit the chamber. The chamber may have a second liquid opening, also preferably located at or near the bottom wall (e.g., in a bottom or side wall) and configured to allow at least liquid to exit the chamber. The chamber is preferably configured such that no gas and/or liquid exit openings in the chamber are closer to the top wall than the air opening. The chamber may be structured to allow uninhibited fluid communication between the air opening and first and second liquid openings. The first and second liquid openings may be located on a same wall or different walls of the chamber. The first and second liquid openings are preferably located below a minimum fluid level.

In exemplary implementations, a bubble trap may include an air outlet connected to an air conduit and in fluid communication with the air opening. The air outlet may be located at or near the top wall of the chamber (e.g., on a side or top wall) and may be connected to an air conduit. The air conduit may consist of an air tube or any other suitable conduit. A valve (e.g., a check valve or other suitable restriction means) may be disposed on the air tube. The valve may be actuated manually, or a controller may be configured to engage the valve to stop fluid flow through the air outlet. The valve may be disposed around or in the air tube. The controller may be any suitable controller, which may include a processor and other suitable electronics to operate software and a valve.

In exemplary implementations, the bubble trap may include a first liquid outlet, preferably located near the top wall of the chamber (e.g., on a side or top wall). The first liquid outlet is connected to a first conduit and in fluid communication with the first liquid opening. The first liquid outlet may be connected to the first liquid opening via, for example, a first channel or tube that runs up a side wall. The bubble trap may include a second liquid outlet, also preferably located near the top wall of the chamber (e.g., on a side or top wall). The second liquid outlet is connected to a second conduit and in fluid communication with the second liquid opening. The second liquid outlet may be connected to the second liquid opening via, for example, a second channel or tube that runs up a side wall. The outlets may be located on a same wall or different walls of the chamber. The air outlet and first and second liquid outlets may preferably, but not necessarily, be disposed on a same side wall of the chamber in substantially a straight line. The chamber may be structured to allow uninhibited fluid communication between the air outlet and first and second liquid outlets.

In exemplary implementations, a perfusion apparatus may include a chamber, a pulsatile pump, and a conduit configured to allow perfusion liquid and any gas entrained in the perfusion liquid to flow from the pump into the chamber under fluctuating flow rate and pressure. For example, inlet pressure may be reduced from a maximum inlet pressure fluctuation (variation) of 350 mmHg peak to peak. For example, maximum outlet pressure fluctuation may be reduced to less than 1.5 mmHg peak to peak. A first outlet conduit connected to a first liquid outlet may be connected to a first area of the organ (e.g., the portal vein of a liver). A second conduit connected to a second liquid outlet may be connected to a second area of the organ (e.g., the hepatic artery of a liver). The chamber may be configured to release gas from the perfusion liquid (e.g., the chamber may function to eliminate bubbles that may be drawn up in an upstream portion of the tubing) and to maintain a minimum volume of gas sufficient to dampen flow rate and pressure fluctuations of the liquid. The minimum volume of gas is defined by at least the volume of the chamber above the air opening.

A method of perfusing an organ may include flowing a perfusion liquid into a chamber under fluctuating flow rate and pressure, maintaining at least a minimum volume of gas in the chamber sufficient to dampen flow rate and pressure fluctuations of the perfusion liquid, allowing the perfusion liquid with reduced flow rate and pressure fluctuations to flow out of the chamber, and perfusing the organ with the reduced-flow-rate-and-pressure-fluctuation liquid. For example, a ratio of the pressure fluctuations of the perfusion liquid flowing into the chamber and pressure fluctuations of the perfusion liquid flowing out of the chamber may be more than 10 to 1, for example, 11 to 1, 50 to 1, 100 to 1, 175 to 1 or even more than 200 or 230 to 1, such as 233 to 1. For example, when the liquid is flowing through the chamber between 0.3 and 2.0 liters per minute, the ratio of the pressure fluctuation of liquid flowing into the chamber and the pressure fluctuation of liquid flowing out of the chamber may be at least 233 to 1. For example, when liquid is flowing into the chamber at about a maximum of 2 liters per minute and the pressure fluctuation of liquid flowing into the chamber is about 350 mmHg peak to peak, the pressure fluctuation of liquid flowing out of the chamber is preferably less than or equal to 2.5 mmHg, such as less than about 2 mmHg, peak to peak.

In exemplary implementations, at least a part of the chamber may be transparent to enable visual assessment of the liquid level in the chamber.

In exemplary implementations, the chamber is operable when the liquid is at temperatures between 3 and 40, such as between 3 and 10, 3 and 5, 20 and 40, 20 and 30, 35 and 37, and the like, degrees Celsius.

In exemplary implementations, all walls of the chamber may be composed of rigid materials. For example, the chamber may be composed of injection molded resin (e.g., SAN (styrene acrynitrile), which is medical grade, nontoxic and biocompatible), transparent polycarbonate, PMMA, ABS, PVC or any other suitable material.

In exemplary implementations, an apparatus for separating gas from a perfusion liquid in a perfusion apparatus may include a bubble trap and a liquid level sensor configured to detect the level of perfusion liquid in the bubble trap. The perfusion apparatus (such as a transporter unit) may include a controller, a valve configured to control flow of at least gas exiting the chamber, and an organ bath configured to retain perfusion liquid. The bubble trap may include a chamber for housing gas and perfusion liquid, and may include an air outlet configured to allow at least gas to exit the chamber. The controller may be configured to control the valve such that if the liquid level sensor senses that a level of the perfusion liquid is too high or too low, the controller controls the valve to open or close the air outlet to start or stop flow of air out of the chamber through the air outlet. For example, if the liquid level sensor senses that a level of perfusion liquid is too low for effective bubble release, for example due to build up of gas released from the perfusion liquid, it may alert the user or a controller to open the air outlet valve to release air from the chamber. During priming, the liquid level sensor may be used to determine when the liquid level approaches a preferred operational level, for example allowing the valve to be closed when the liquid level is near, just below, or just above the preferred operational level. For example, the preferred operational level of liquid in the chamber may be between 1 and 15 mm below the bottom of the air outlet, preferably between 5 and 10 mm below the bottom of the air outlet, and more preferably about 8-9 mm below the bottom of the air outlet. When the valves disposed on tubes connected to the first and second liquid openings are open, the air outlet valve may be closed. When the air outlet valve is open, it may be exhausting only gas into the organ basin. The sensor may be a Hall effect sensor that works in concert with a magnet, or any other suitable sensor contemplated by a skilled artisan. For example, the liquid level sensor system may include a magnet in a float that is buoyant in the perfusion liquid. Whether the air outlet valve is open or closed is dependent on the location of the magnet in relation to the Hall effect sensor.

A method of priming a perfusion apparatus for perfusing an organ or tissue may include flowing a perfusion liquid through a chamber, and sensing if the perfusion liquid has reached the preferred operational level in the chamber. When the preferred operational level has been achieved, the air outlet valve may shut off. When the air outlet valve is shut off, the valves disposed on the tubes connected to the first and second liquid openings may be open to allow priming of the downstream tubes.

In exemplary implementations, the apparatus may include one or more bubble sensor(s) configured to detect the presence of gas in liquid exiting the chamber. The bubble sensor may be disposed on at least one conduit downstream of the bubble trap. For example, the bubble sensor may send a signal to the controller when an unacceptable size or number of bubbles is detected, and the controller may stop the perfusion of liquid by stopping the pump and/or controlling a valve (e.g., a pinch valve or other suitable valve) disposed on the at least one perfusate conduit, for example downstream of the bubble trap. Flow may be resumed after bubbles in the liquid exiting the chamber are removed.

Preferably, the bubble sensor is an ultrasonic sensor disposed around tubing, although any suitable sensor may be used. Ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles in the tubing.

In exemplary implementations, apparatus for separating gas from perfusion liquid for perfusing an organ may include a chamber for housing the gas and perfusion liquid. The chamber may include an inlet configured to allow at least one of gas or perfusion liquid to flow into the chamber, a liquid outlet and a sampling port configured to allow a liquid sample to be continuously or periodically withdrawn from the chamber. The sampling port may have a first end located on the top wall of the chamber and configured to allow the liquid sample to be extracted. In embodiments, the sampling port may extend to a second end at or near the bottom wall of the chamber, and the second end may be configured to allow the perfusion liquid to enter the sampling port to be extracted from the first end. The first end of the sampling port may include a luer fitting, threaded cap, septum, or other suitable closing means. A cover may be configured to seal the first end of the sampling port. The sampling port may be configured to not contact any of the side walls of the chamber. Alternatively, the sampling port may be configured to contact or be integral with one of the side walls of the chamber. The sample port may be located in other areas of the fluid path other than the chamber.

A method of perfusing an organ may include flowing a perfusion liquid through the bubble trap, preferably in a recirculating circuit, and withdrawing a sample of the perfusion liquid in a single event, periodically or continuously. The sample may preferably be withdrawn from near the liquid exit outlet, such as at or near the bottom portion of the chamber of the bubble trap, to be most representative of the perfusion liquid that will enter the organ.

Figure 2:
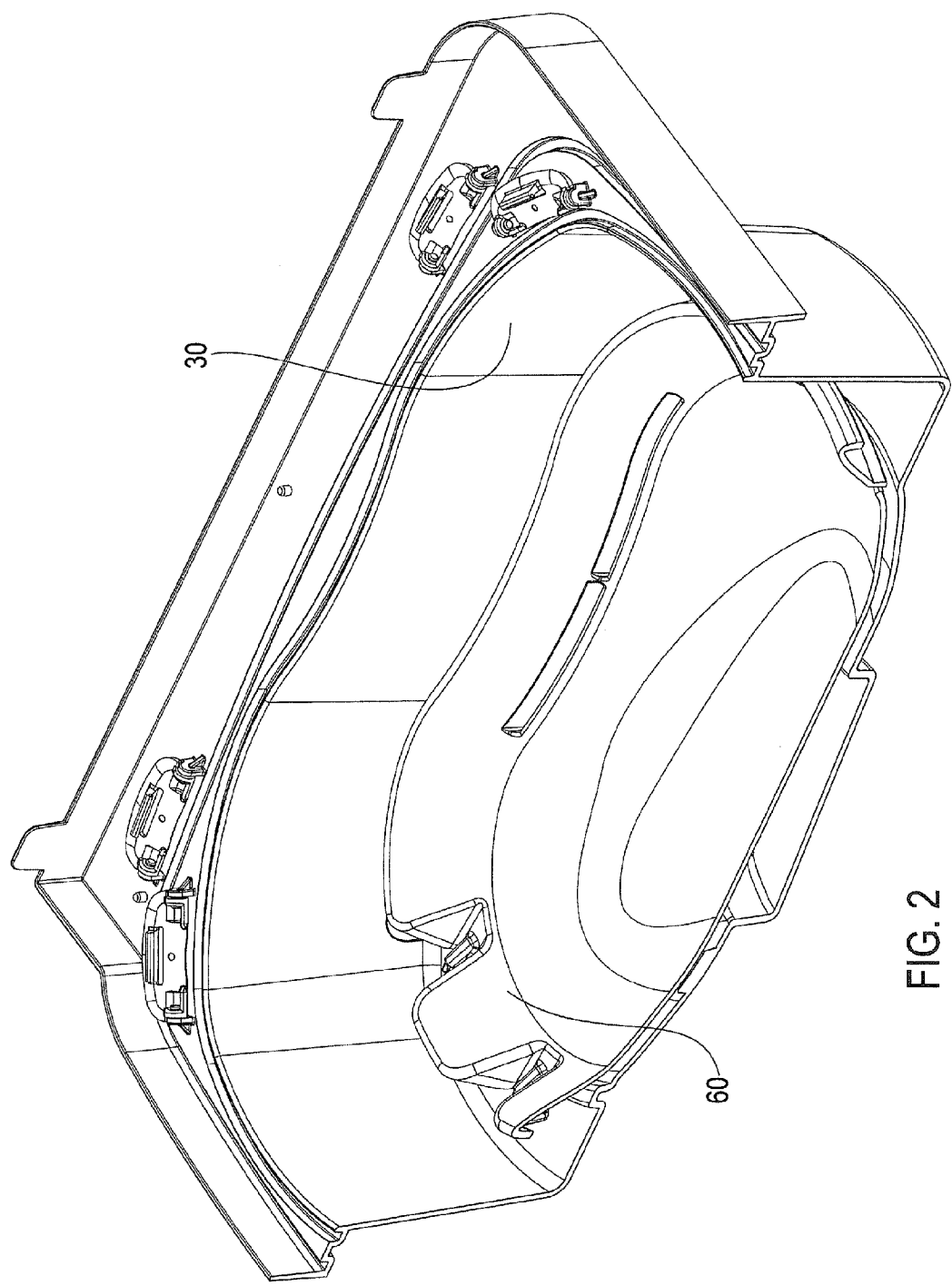
FIG. 2 is a perspective view of an exemplary cradle and basin that may be used in perfusion apparatus of FIG. 1.

FIG. 1 is a schematic diagram of a perfusion apparatus, such as a transport and/or storage apparatus, 10 for an organ 20. The organ 20 may preferably be a liver or kidney but may be any human or animal, natural or engineered, healthy, injured or diseased organ or tissue, including heart, lungs, intestine, or other organ or tissue. The depicted apparatus includes a basin 30 in which the organ 20 may be placed. As shown in FIG. 2, the basin 30 may hold a cradle 60, which preferably includes a surface on which the organ 20 is preferably disposed when the organ 20 is in the apparatus 10. The basin 30 may include a first filter that can function as a gross particulate filter. The basin 30 and/or the cradle 60 are preferably configured to allow a perfusate bath to form around the organ 20. As shown in FIG. 1, the basin 30 may also include a temperature sensor 40 located in or near the cradle 60. The basin may include multiple temperature sensors 40, which may provide redundancy in the event of a failure and/or may provide temperature measurement at multiple locations. Preferably, the temperature sensor(s) 40 is an infrared temperature sensor. The temperature sensor(s) 40 is preferably disposed as close as practical to the organ 20 when the organ 20 is disposed in the cradle 60 in order to improve the usefulness and accuracy of the temperature sensor(s) 40, which preferably provides a temperature measurement of the perfusate that may be correlated to a temperature of the organ 20. Alternatively or additionally, the temperature sensor(s) 40 may be used to directly measure the temperature of the organ 20.

The basin 30 is preferably disposed within a coolant container 50 that may contain cold materials such as ice, ice water, brine or the like. Coolant container 50 may be permanently or removably attached to, or an integral, monolithic part of, apparatus 10. Thus, in use, the organ 20 is disposed within the cradle 60 and/or the basin 30, which is disposed within a compartment defined by the coolant container 50. Preferably, each of the basin 30, cradle 60 and coolant container 50 is configured, or keyed, to fit with its corresponding mating component in a single orientation. The configuration of the coolant container 50, basin 30 and cradle 60 may provide a configuration that provides cooling for the organ 20 without the contents of coolant container 50 contacting the organ 20 or the cradle 60. Although the coolant container 50 is described herein as containing ice, any suitable cooling medium can be used. Ice may be preferable due to the ease with which ice can be procured, but one of ordinary skill would understand that any suitable cooling medium, which could be an active cooling medium (such as a thereto electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle 60 may include components configured to securely restrain the organ 20 in place. Such components may, for example, include user selectable netting that is fastened to the cradle 60.

After passing through the first filter, the perfusate flows along a first flow path 70 that includes a suitable fluid conduit 72, such as flexible or rigid tubing, a pump 80, a pressure sensor 90, a second filter, an optional oxygenator 100 and a bubble trap 110, each of which is discussed below.

The first filter is preferably a relatively coarse filter (relative to the second filter). Such a coarse filter may be provided to prevent large particles, which may for example be byproducts of the organ or of the organ being removed from the donor, from entering and clogging fluid paths of the apparatus 10. The first filter may be an integral part of the basin 30 or the first filter may be disposed elsewhere in the first flow path 70 downstream of the basin 30. The first filter may also be a separate component from the basin 30 or disposed within the fluid conduit 72.

The first flow path 70 may also include a pump 80. The pump 80 may be any pump that is suitable in connection with perfusing of organs. Examples of suitable pumps may include hand operated or motor-operated pumps, such as centrifugal pumps or roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow rate and pressure out of the roller pump that is relatively less pulsatile than would be the case with a single roller. Such a multiple channel roller pump may achieve a constant flow rate and pressure or a minimally pulsatile flow rate and pressure, which may be advantageous depending on the other components in the flow path and/or the type of organ being perfused.

The flow path 70 may include a pressure sensor 90. The pressure sensor 90 may preferably be disposed after the outlet of the pump 80 in order to monitor and/or be used to control the pressure produced at the outlet of the pump by way of a suitable controller 400. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump), or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow rate and pressure and/or provide a sample port. The bubble trap 110 may include a volume of gas, initially or through the accumulation of gas from bubbles that rise and pop to release gas, such that flow rate and pressure fluctuations in the perfusate are dampened or eliminated.

Figure 3:
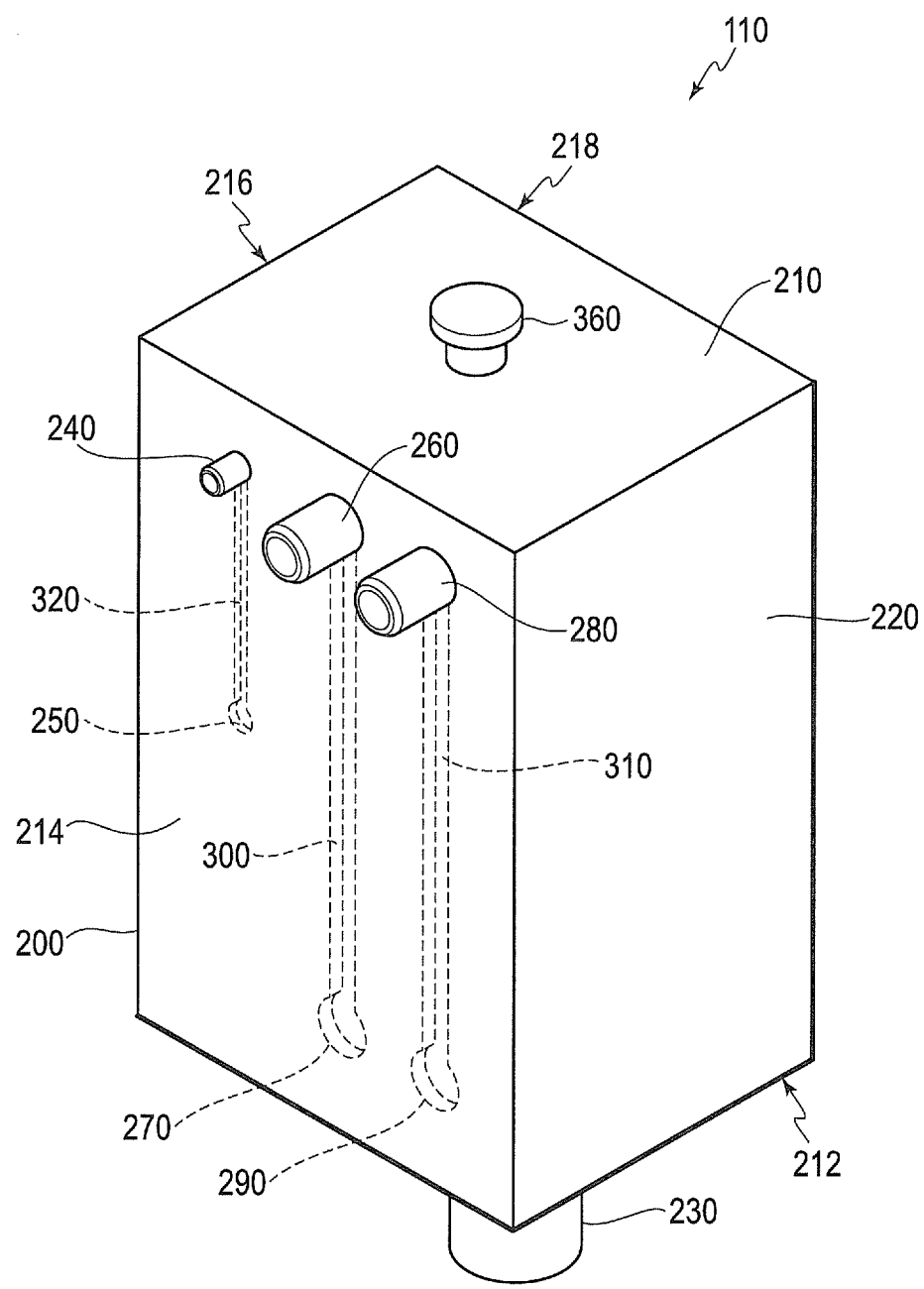
FIG. 3 is a perspective view of external components of an exemplary bubble trap.

As shown in FIG. 3, the bubble trap 110 may comprise a chamber 200 having a top wall 210, a bottom wall 212 and side walls 214, 216, 218, 220. The chamber 200 may have an inlet 230 that allows gas and/or liquid to enter the chamber 200. The inlet 230 may preferably be located in or near the bottom wall. The inlet 230 may be connected to a conduit that is connected to the pump 80.

The bubble trap 110 may have any number of outlets as needed for a given application of the perfusion apparatus. As shown in FIG. 1, a first liquid outlet 260, a second liquid outlet 280 and an air outlet 240 are shown connected to three different flow paths, which may be particularly suited for the perfusion of a liver or any other organ or tissue with multiple blood vessels, or for perfusion of multiple organs or tissue simultaneously. For example, when perfusing a liver, the first liquid outlet 260 is connected to the portal flow path 120 (which is connected to the portal vein of the liver), the second liquid outlet 280 is connected to the hepatic flow path 130 (which is connected to the hepatic artery of the liver), and the air outlet 240 is connected to the bypass flow path 140 (which provides a return path to the basin 30).

The chamber 200 may have an air opening 250 that allows gas to exit. The air outlet 240 of the bubble trap 110 may allow purging of gas through the air opening 250 during a priming or purging process. The air outlet 240 may be connected to or part of purge flow path 140. The air outlet 240 is preferably open during a start-up process so that any air or other gas may be purged from the perfusate path 70. Once the gas is purged from the perfusate path 70, the air outlet 240 may preferably be closed. The air outlet 240 may be closed manually or may be closed automatically by way of a suitable controller 400.

Bypass flow path 140 may include a valve 142, and/or sensors such as oxygen sensor 144 and pH sensor 146. The oxygen sensor 144 and pH sensor 146 may alternatively be disposed on the portal flow path 120 and/or the hepatic flow path 130, or all of or any combination of the bypass flow path 140, the portal flow path 120 and the hepatic flow path 130. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, optionally continuously, to monitor perfusate properties in real time. For the latter use, the liquid level sensor 112 could be used to allow the user, or controller, to maintain the liquid level in the chamber 200 in a predetermined range around air opening 250.

The air opening 250 may preferably be located on side wall 214 of the chamber 200, and between the top wall 210 and the bottom wall 212. The air opening 250 may be connected to and in fluid communication with the air outlet 240 via an air channel 320, which may preferably extend in a vertical direction.

The chamber 200 may have a first liquid opening 270 and a second liquid opening 290 that allow liquid to exit the chamber. The first liquid opening 270 and second liquid opening 290 may preferably be located on a same side wall 214 and at or near the bottom wall 212. The first liquid opening 270 may be connected to and in fluid communication with the first liquid outlet 260 via a first channel 300. The second liquid opening 290 may be connected to and in fluid communication with the second liquid outlet 280 via a second channel 310. The chamber 200 may preferably be structured such that there is uninhibited fluid communication between the inlet 230, air opening 250, first liquid opening 270 and second liquid opening 290.

The chamber 200 may be polygonal and/or curved at the top wall 210. For example, the chamber 200 may be rectangular, square, round or other suitable shape in cross-section. The chamber 200 may be substantially L-shaped at the top wall 201, wherein one corner of the rectangular-shaped top wall 210 may be folded into the center of the chamber 200. The chamber 200 may have uniform or non-uniform cross-sectional dimensions. For example, it may be wider at the top and narrower at the bottom. The inlet 230 may be disposed on the bottom wall 212 at a higher position than the lowermost portion of the chamber 200. The level sensor 112 (described in more detail below) may be disposed on the same or a different side wall than the air opening 250, first liquid opening 270 and/or second liquid opening 290. For example, the level sensor 112 may be disposed on the side wall 216 adjacent to the side wall 214 on which the air opening 250, first liquid opening 270 and second liquid opening 290 are located. The relative direction (e.g., top/bottom) of the walls of the chamber 200 are defined when the bubble trap 110 is in an at rest position in the perfusion apparatus 10.

In embodiments, the perfusate is preferably acellular fluid, for example, fluid that is not blood.

In embodiments, at least part of the chamber 200 may be transparent so that a doctor or clinician can visually inspect the fluid level in the chamber 200.

In embodiments, the chamber 200 may be designed to be operable when the fluid is between 3 and 5, and/or between 20 and 30, and/or between 35 and 38 degrees Celsius. This is advantageous because such hypothermic, midthermic, and/or normothermic conditions, respectively, may result in better preservation of various organs.

In embodiments, the chamber 200 may be composed of rigid materials. A rigid material is, for example, a material that inflexible and not deformable under normal operating conditions. For example, the chamber may be composed of injection molded resin (e.g., SAN (styrene acrynitrile), which is medical grade, nontoxic and biocompatible), transparent polycarbonate, PMMA, ABS, PVC or any other suitable material.

Bubble sensors 124, 134 may be disposed downstream to detect whether gas bubbles are present in the perfusate flowing out of the first liquid outlet 260 and/or the second liquid outlet 280. Valves may be disposed as a redundancy on tubes connected to the first liquid outlet 260 and second liquid outlet 280, and may be used, for example, to prevent fluid from exiting the chamber 200 when a bubble sensor 124, 134 detects gas in perfusate exiting the bubble trap 110. The valves may be pinch valves or any other suitable valves.

A level sensor 112 may detect the level of the liquid in the chamber 200 of the bubble trap 110. In addition to its functions described below, the level sensor 112 may be utilized as a redundant method to further reduce the risk of air bubbles being sent downstream into the portal flow path 120 and the hepatic flow path 130. The level sensor 112 is preferably disposed along a side wall of the chamber 200. The level sensor 112 may be an integral component of the bubble trap 110, or alternatively may be disposed in whole or in part elsewhere within the apparatus 10. The controller 400 may receive a signal from the level sensor 112 indicative of the level of the liquid inside the chamber 200. The liquid level sensor 302 may include, for example, a magnet in a float that works in concert with a Hall effect sensor, or other suitable sensor. The liquid level sensor 302 may be configured, for example, to detect the level of a float on the liquid along the side wall 216 inside the chamber 200. In this configuration, the float may preferably be an integral component of the chamber 200 and a Hall effect sensor may be separate from the bubble trap 110, thus making the float disposable and the Hall effect sensor re-useable.

The bubble trap 110 may include valves disposed on the tubes connected to the air outlet 240, the first liquid outlet 260 and the second liquid outlet 280. During the priming process, if the liquid level sensor 112 detects that the liquid inside the chamber 200 is below a preferred operational level, the controller 400 may control the valve on the tube connected to the air outlet 240 to allow gas to exit the chamber, and may control valves 122,132 on the tubes connected to the first liquid outlet 260 and second liquid outlet 280 to shut off fluid flow out of the chamber 200. This allows the liquid in the chamber to reach a preferred operational level. The operational level may be when the level of liquid reaches a point just below the level of the air opening 250. For example, the preferred operational level of liquid in the chamber may be between 1 and 15 mm below the bottom of the air outlet, preferably between 5 and 10 mm below the bottom of the air outlet, and more preferably about 8-9 mm below the bottom of the air outlet. When the level sensor 112 detects that the liquid in the chamber 200 is at or above the preferred operational level, the controller may control the valve on the tube connected to the air outlet 240 to shut off flow out of the chamber 200, resulting in a chamber 200 with at least a predetermined minimum volume of gas. Once the priming process is complete (e.g., when the preferred operational level is achieved), the controller 400 may shut off gas and/or liquid flow out of the chamber through air outlet 240, for example, by engaging a valve (or other suitable restriction means) disposed on a tube connected to the air outlet 240.

Alternatively, or in addition, the bubble trap 110 may be operated during a priming process by flowing the liquid through the chamber 200 and into the organ 20 and sensing if the liquid is flowing out of the air outlet 240 in the chamber 200. If the liquid is sensed to be flowing out of the air outlet 240, the controller 400 may shut off the air outlet (e.g., through the use of a suitable valve).

The level sensor 112 may optionally be used during the purging process to determine when the wash is complete and/or may be used to determine when the purging process needs to be repeated, which may happen after bubbles have been detected, for example, in a downstream tube.

The bubble trap 110 may be configured to reduce flow rate and pressure fluctuations of liquid flowing out of the first liquid outlet 260 and/or the second liquid outlet 280. Through the use of the level sensor 112 and the air outlet 240, the accumulator function of the bubble trap can be tuned to account for differing amplitudes and frequencies of pulsatility in the perfusate flow rate and pressure. For example, as shown in FIGS. 5A-5E, the bubble trap 110 may be operated by flowing liquid into the chamber 200 with fluctuating flow rate and pressure, maintaining at least a minimum volume of gas in the chamber 200 sufficient to dampen flow rate and pressure fluctuations of the liquid, allowing the liquid with the reduced flow rate and pressure fluctuations to flow out of the chamber 200, and perfusing the organ 20 with the reduced-flow-rate-and-pressure-fluctuation liquid.

Figure 6A:
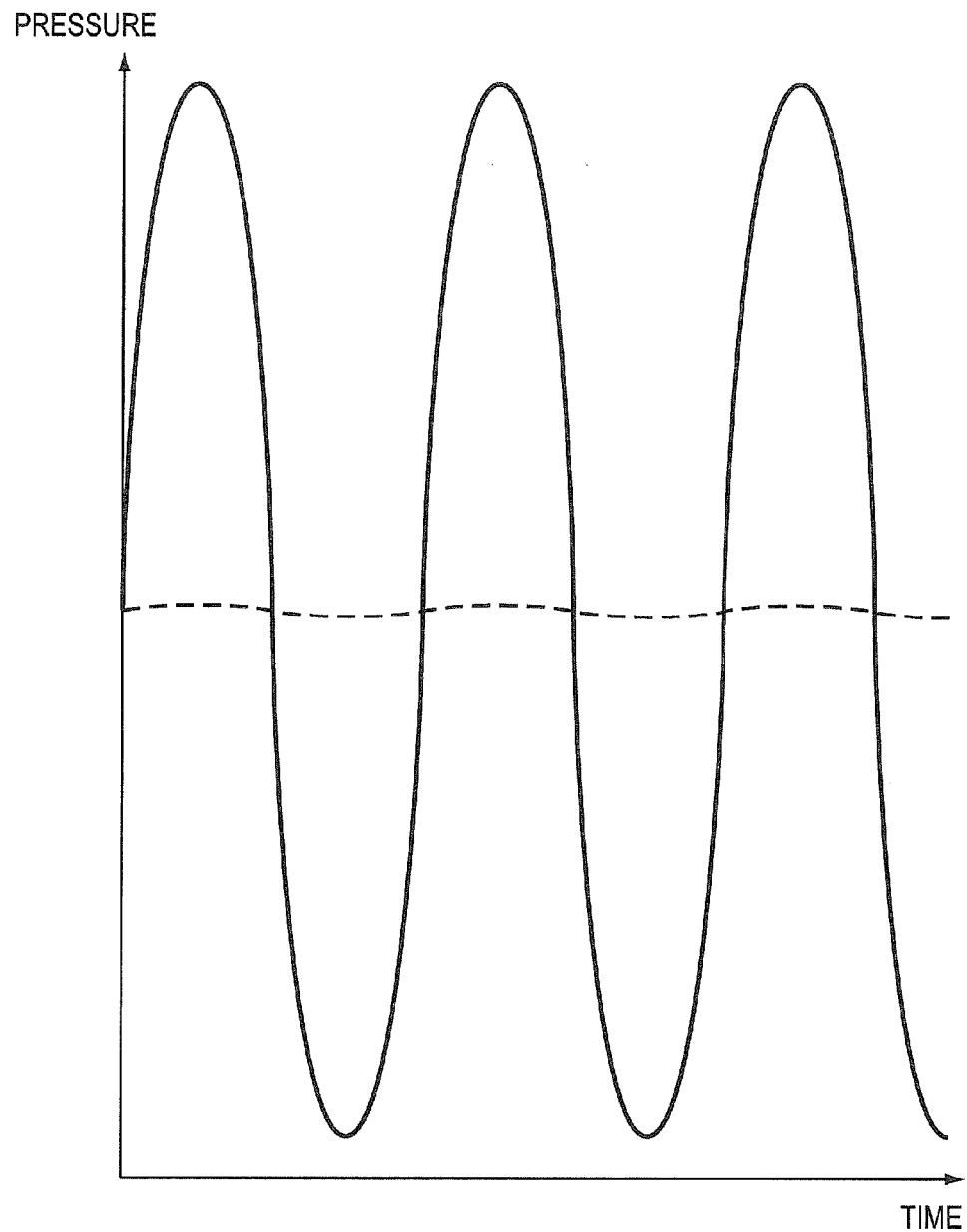
FIG. 6A is an idealized representation of a graph comparing pressure fluctuations of liquid flowing into the chamber and pressure fluctuations of liquid flowing out of the chamber of an exemplary bubble trap.
Figure 6B:
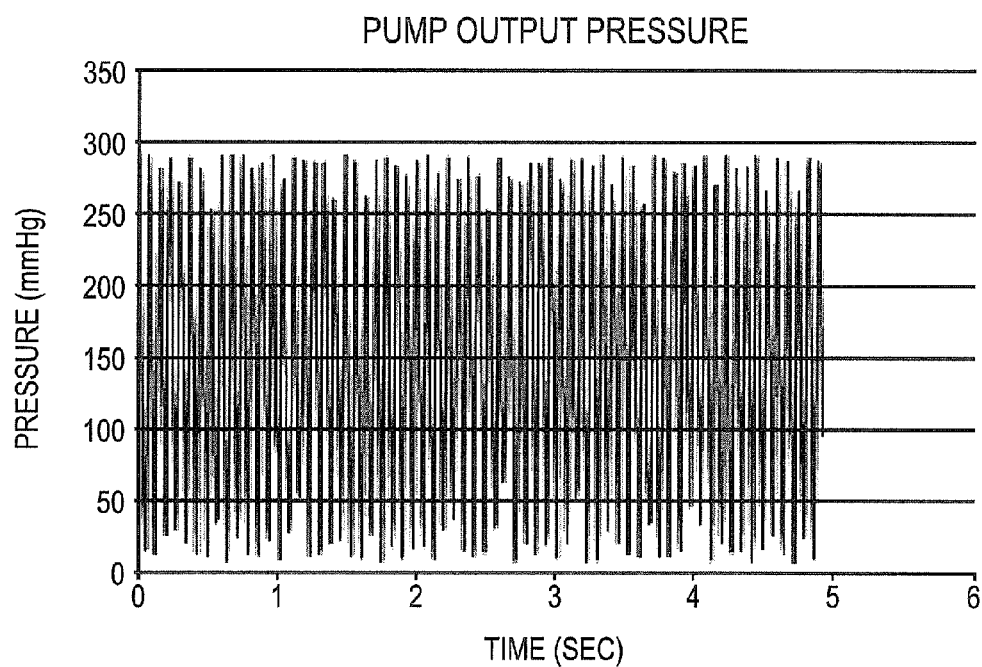
FIGS. 6B and 6C are graphs displaying sample data of inlet pressure fluctuations and outlet pressure fluctuations of the chamber of an exemplary bubble trap.
Figure 6C:
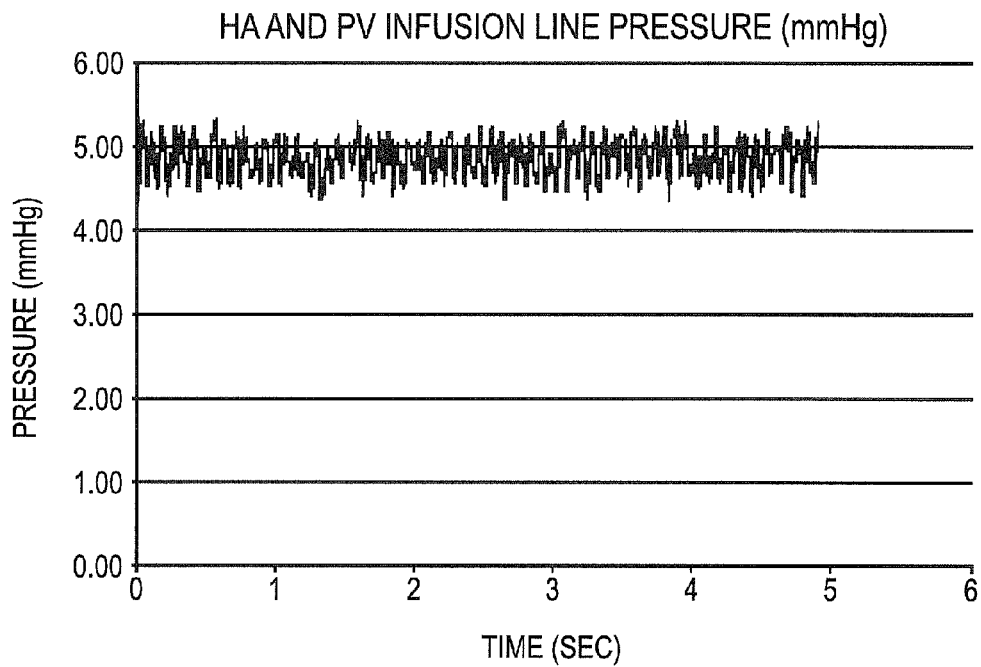

The combination of the range of liquid held in the chamber 200 (for example, between 0.1 liters to 0.2 liters of fluid, as discussed below in Example 1) and the minimum volume of compressible gas in the chamber 200 may result in dampening of flow rate and pressure fluctuations of the liquid (caused by, for example, the pulsatile flow rate generated by the pump 80) as the liquid flows into the chamber 200 via the inlet 230. For example, the ratio of the pressure fluctuation of the liquid flowing into the inlet 230 and the pressure fluctuation of the liquid flowing out of the first liquid outlet 260 and/or the second liquid outlet 280 may be more than 10 to 1, for example, 11 to 1, 50 to 1, 100 to 1, 150 to 1, 175 to 1 or more than 200 or 230 to 1, such as 233 to 1. For example, as shown in FIGS. 6A-6C, when the pressure fluctuation of the liquid flowing into the inlet 230 is about 350 mmHg peak to peak, the pressure fluctuation of the liquid flowing out of the first liquid outlet may be controlled to be less than or equal to 2 mmHg peak to peak by maintaining a suitable volume of air in the chamber 200.

Figure 4:
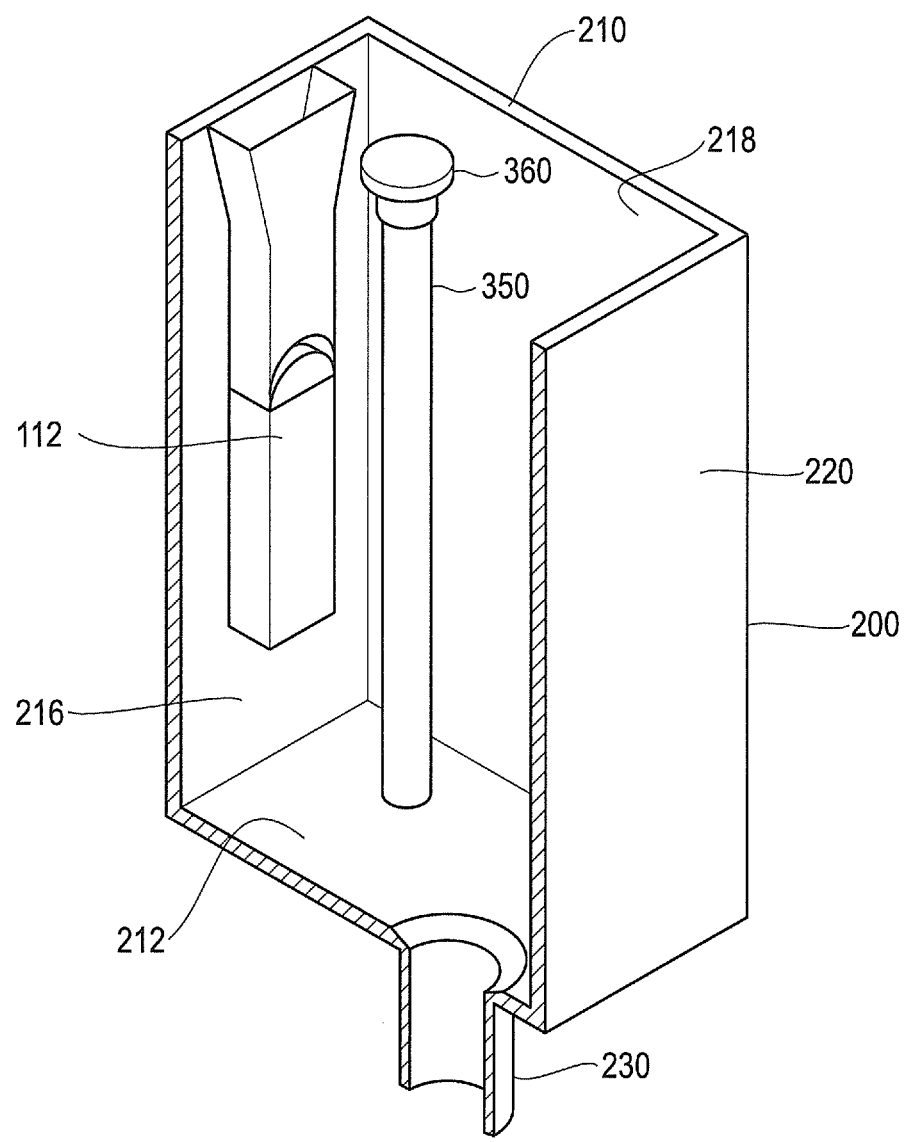
FIG. 4 is a cross-sectional perspective view of internal components of the bubble trap of FIG. 3.
Figure 5A:
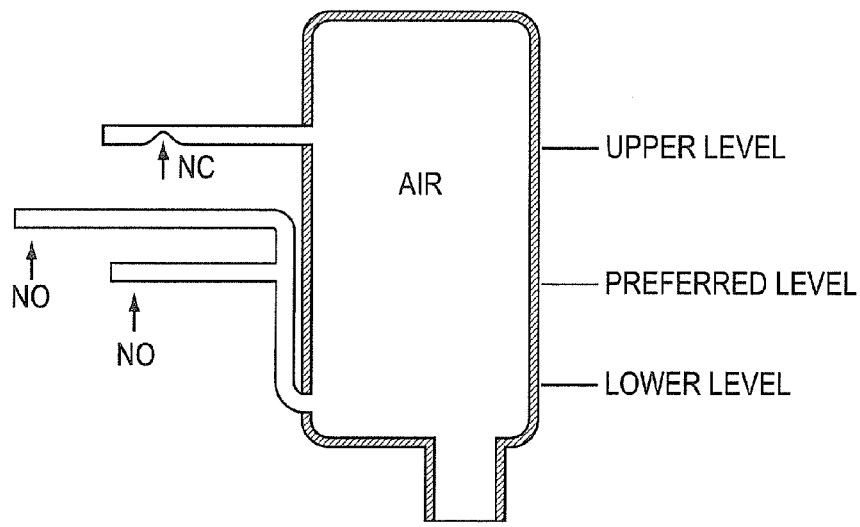
FIGS. 5A and 5B are diagrams of the liquid and gas path within a bubble trap when liquid first enters the chamber.
Figure 5B:
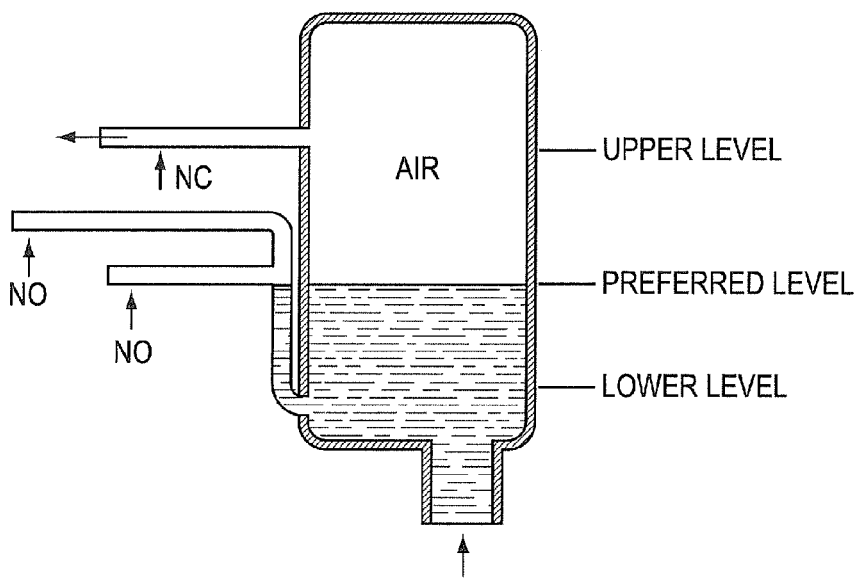
Figure 5C:
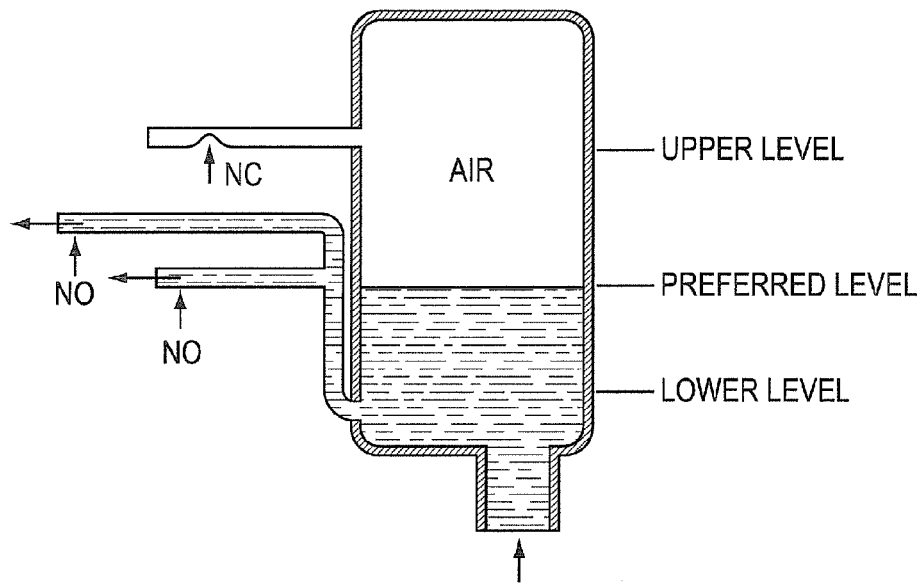
FIGS. 5C-5E are diagrams of the liquid and gas path within the bubble trap of FIGS. 5A and 5B when the liquid reaches preferred as well as upper/lower fluid levels.
Figure 5D:
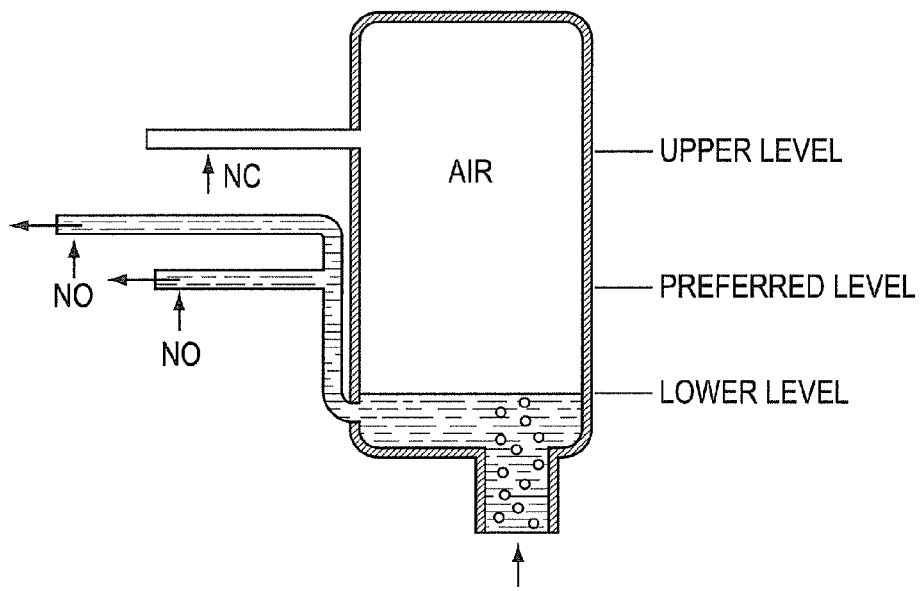
Figure 5E:
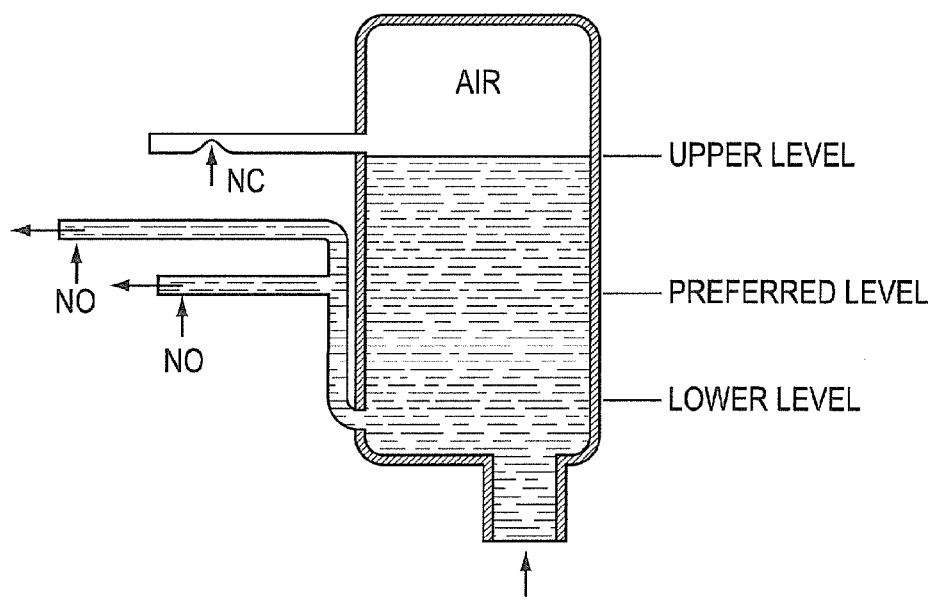

As shown in FIGS. 3 and 4, the bubble trap 110 may include a sampling port 350, preferably with a first end located at or near the top wall 210 of the chamber 200 and a tube 306 that extends to a second end near the bottom wall 212. The sampling port 350 may be configured to allow a liquid sample to be withdrawn from the chamber, for example, in a single event, periodically or continuously. The first end of the sampling port 350 may allow for the liquid sample to be extracted, and may have a luer fitting, threaded cap, septum or other suitable fitting to assist in maintaining sterility. This may be useful for a doctor or clinician to obtain samples of the perfusate for analysis at any time. The port may also be utilized by a user to administer substances to the perfusate without opening the basin, which may be a safer and more convenient approach than opening lids of the disposable portion of the apparatus 10 and breaching the sterile barrier. The bubble trap 110 may also include a cover 360 that seals the first end of the sampling port 350. In a method of perfusing the organ 20, the sampling port may be used to withdraw a liquid sample from the bubble trap 110, the liquid sample not being used to perfuse the organ.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Flow control clamps 127, 137 may be used to fine-tune the flow rate in one or both of portal flow path 120 and hepatic flow path 130. Preferably, the organ provides self-regulation to control an amount of flow that is divided between the portal flow path 120 and the hepatic flow path 130. In such self-regulated flow, pressure sensors 128, 138 provide overpressure monitoring. In the event that flow rate and pressure delivered to the organ in either or both of the portal flow path 120 or the hepatic flow path 130 exceed a predetermined threshold, the apparatus 10 can manually or automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold.

After exiting one or both of the portal flow path 120 and hepatic flow path 130, perfusate flows through the organ and returns to the basin 30 to form an organ bath.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. By implementing such monitoring, misuse or potentially inappropriate conditions of the apparatus 10 can be detected and optionally recorded and/or transmitted to a monitor.

The apparatus 10 may include storage compartments for items other than the organ 20. For example, the apparatus 10 may include a document compartment to store documents and/or charts related to the organ 20. The apparatus 10 may include one or more sample compartment. The sample compartment(s) may be configured, for example, to store fluid and/or tissue samples. The sample compartment(s) may be advantageously disposed near the coolant container 50 to provide cooling, which may be similar or equivalent to the cooling provided for the organ 20.

The apparatus 10 may include one or more tamper evident closures. A tamper evident closure may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

The bubble trap 110 and any tubes or other components that come into contact with the perfusate are preferably disposable. Disposable components may preferably be sterilized prior to use. These sterilized, disposable components may be sold in one or more sterilized disposable kit or saleable package as a unit. This allows the sterilized, disposable components to be "single-use" components. That is, once an organ 20 has been placed inside of the basin 70 and used, such sterilized, disposable components may be discarded without being used for another organ. Accordingly, the organ perfusion apparatus 10 maintains strict sterility and prevents contamination of an organ 20 being perfused, transported, and/or stored in the apparatus 10. The components of the apparatus 10 that are not disposable may be reused indefinitely. Preferably, all components that contact perfusate and/or the organ 10 are disposable. In exemplary implementations, the tubing, filter, oxygenator and bubble trap are packaged together in a manner preconfigured to be placed into a flow path arrangement of fixed-location parts in apparatus 10, and the cradle and basin are packaged individually or together, and optionally together with the tubing, filter, oxygenator and bubble trap.

Example 1

Using an apparatus of FIG. 1, the chamber 200 of the bubble trap 110 has a total volume of about 0.7 liters. The chamber 200 holds between 0.1 and 0.163 liters of liquid in use. The chamber 200 holds between 0.537 and 0.6 liters of gas in use. The volume of gas above the air opening 250 is between 76% to 95% of the total volume of the chamber. For example, if the chamber 200 has 0.1 liters of liquid in use, the volume of gas above the air opening 250 is 86% of the total volume of the chamber. Alternatively, if the chamber 200 has 0.163 liters of liquid in use, the volume of gas above the air opening 250 is 76% of the total volume of the chamber. The pump operates such that the liquid flows into the chamber at a maximum rate of about 2.0 liters per minute. The pump tube segment inner diameter is about 0.313 inches, and the outer diameter is about 0.437 inches. The pump rotor diameter is about 4.0 inches, and contains four rollers equally spaced around the circumference of the rotor, each roller being about 0.47 inches in diameter. The pressure fluctuation of liquid flowing into the inlet 230 is dependent on the RPM of the rotor, and at the maximum flow rate of 2.0 liters per minute, the pressure may fluctuate between about 230 mmHg to about 350 mmHg. At lower RPMs, the pressure fluctuations may be lower. The pressure fluctuation of liquid flowing out of the first liquid outlet 260 and/or the second liquid outlet 280 is equal to or less than 2 mmHg peak to peak at the maximum flow rate of 2.0 liters per minute. The chamber is maintained at a temperature between 3 and 5 degrees Celsius during operation of the perfusion apparatus; this temperature results from the chamber's contact with the basin 30 in the coolant container 50.

What has been described and illustrated herein are preferred exemplary implementations of the invention along with some variations. The terms, descriptions and figures used herein are set forth by way of illustration only and are not meant as limitations. Those skilled in the art will recognize that many variations are possible within the spirit and scope of the invention.

What is claimed is:

1. A perfusion apparatus comprising:
   a pulsatile pump;
   a bubble trap comprising a chamber having at least one liquid inlet opening, only a single gas outlet opening, and at least one liquid outlet opening;
   a controller in communication with the pump and the bubble trap;
   a conduit forming a liquid path between the pump and the liquid inlet opening of the chamber; and
   a conduit forming a liquid path between the liquid outlet opening and an organ container;
   wherein:
   a volume of the chamber above the gas outlet opening when the perfusion apparatus is in an upright rest position is at least 75% of a total volume of the chamber, and;
   the controller is configured to maintain a level of liquid in the chamber, during normal operation of the bubble trap, between 1 mm and 15 mm below the bottom of the gas outlet opening.

2. The apparatus according to claim 1, wherein the controller is configured to maintain a ratio of pressure fluctuation of perfusion liquid flowing into the inlet opening to pressure fluctuation of perfusion liquid flowing out of the liquid outlet opening to more than 10 to 1.

3. The apparatus according to claim 2, wherein the ratio is at least 100 to 1.

4. The apparatus according to claim 3, wherein the ratio is at least 200 to 1.

5. The apparatus according to claim 1, wherein the total volume of the chamber is about 0.5 to 1 liter.

6. The apparatus according to claim 1, wherein the bubble trap further comprises a sampling port extending from a top wall of the bubble trap to a sampling port inlet located near a bottom wall of the bubble trap.

7. The apparatus according to claim 1, wherein the bubble trap further comprises a liquid level sensor configured to detect a level of perfusion liquid in the bubble trap.

8. The apparatus according to claim 1, wherein a volume of gas in the chamber is at least 75% of the total volume of the chamber.

9. The apparatus according to claim 8, wherein the chamber also contains a perfusion liquid.

10. The apparatus according to claim 1, wherein the controller is configured to maintain at least a minimum volume of gas in the chamber that is sufficient to dampen pressure fluctuations of perfusion liquid flowing into the liquid inlet opening.

11. The apparatus according to claim 10, wherein the controller is configured to maintain the volume of gas in the chamber by controlling at least one of the liquid inlet opening, the gas outlet opening, and the liquid outlet opening.

12. The apparatus according to claim 10, wherein the minimum volume of the gas in the chamber maintained by the controller is at least 75% of the total volume of the chamber.

13. The apparatus according to claim 1,
   wherein the liquid inlet opening is disposed at a bottom of the chamber,
   wherein the gas outlet opening is disposed above the liquid inlet opening, and
   wherein a top of the container opposite the bottom is disposed above the gas outlet opening.

14. The apparatus according to claim 1, wherein the chamber includes liquid at a level, during normal operation of the bubble trap, between 1 mm and 15 mm below the bottom of the gas outlet opening.

15. A method of perfusing an organ or tissue, the method comprising perfusing the organ or tissue with perfusion liquid that has passed through the apparatus of claim 1.

* * * * *